United States Patent [19] [11] 4,178,455
Hirai et al. [45] Dec. 11, 1979

[54] PROCESS FOR PREPARING AROMATIC URETHANES

[75] Inventors: Yutaka Hirai; Katsuharu Miyata; Makoto Aiga; Seiji Hasegawa, Omuta, all of Japan

[73] Assignee: Mitsui Toatsu Chemicals, Incorporated, Tokyo, Japan

[21] Appl. No.: 925,543

[22] Filed: Jul. 17, 1978

[30] Foreign Application Priority Data

Jul. 25, 1977 [JP] Japan ................... 52-88441
Jul. 28, 1977 [JP] Japan ................... 52-89805

[51] Int. Cl.$^2$ .................................. C07C 125/04
[52] U.S. Cl. ................................ 560/24; 560/25
[58] Field of Search ........................... 560/24, 25

[56] References Cited

U.S. PATENT DOCUMENTS

| 3,956,360 | 5/1976 | Zajacek et al. | 560/24 |
| 3,993,685 | 11/1976 | Zajacek et al. | 560/24 |
| 4,080,365 | 3/1978 | Hirai et al. | 560/25 |

FOREIGN PATENT DOCUMENTS 1087896 10/1967 United Kingdom ................ 560/24

*Primary Examiner*—James O. Thomas, Jr.
*Assistant Examiner*—G. T. Breitenstein

[57] ABSTRACT

In a process for preparing an aromatic urethane which comprises reacting an aromatic nitro compound, an organic compound containing at least one hydroxyl group, and carbon monoxide at elevated temperature and pressure in the presence of a catalytic system composed of a catalyst consisting of a platinum metal, a platinum metal compound, and/or a platinum metal compound-containing compound and a promoter consisting of a Lewis acid and/or a Lewis acid-containing compound, an organic primary amino compound, a urea compound, a biuret compound, an allophanate compound, or a mixture thereof is added to the reaction system whereby the reaction rate is increased and the yield of the desired product is enhanced. For example, 2,4-diethylcarbamatetoluene can be prepared in quantitatively high yield by reacting 2,4-dinitrotoluene, ethanol, carbon monoxide, and a small amount of aminonitrotoluene at elevated temperature and pressure in the presence of palladium chloride and ferrous chloride-pyridine complex.

38 Claims, No Drawings

PROCESS FOR PREPARING AROMATIC URETHANES

BACKGROUND OF THE INVENTION

1. Field of the Invention

This invention relates to improvements in the preparation of aromatic urethanes. More particularly, it relates to an improved process for preparing an aromatic urethane (hereinafter referred to simply as "urethane") which comprises reacting an aromatic nitro compound, an organic compound containing at least one hydroxyl group (hereinafter referred to simple as "hydroxyl-containing compound"), and carbon monoxide at elevated temperature and pressure in the presence of a catalytic system composed of a catalyst consisting of a platinum metal, a platinum metal compound, and/or a platinum metal compound-containing compound and a promoter consisting of a Lewis acid and/or a Lewis acid-containing compound.

2. Description of the Prior Art

Urethanes have heretofore been produced mainly by reaction of isocyanates with alcohols. In recent years, the production of isocyanates has become difficult partly due to the lack and rising costs of starting materials therefor and partly due to the high toxicity of intermediate formed during the manufacture of isocyanates. Consequently, there have been developed and proposed many novel processes for the preparation of urethanes without using any isocyanate. However, these newly developed processes involve several serious problems and have not yet been put into practice on an industrial scale.

For example, U.S. Pat. No. 3,338,956 describes a process wherein urethanes are prepared from alcohols, carbon monoxide, and nitro compounds with the aid of a rhodium chlorocarbonyl catalyst. However, this process is not economically advantageous in the preparation of highly pure urethanes because the desired product is obtained only in low yield even if the urethanation reaction is carried out for a long period of time in the presence of a large amount of the catalyst.

There has been proposed another process in which urethanes are prepared by reacting organic hydroxyl-containing compounds, carbon monoxide, and nitro compounds in the presence of a metal of Group VIII of the Periodic Table combined with a promoter comprising a salt of a metal capable of existing in two or more valence states (German Pat. No. 1,543,051). However, this process is useless from an industrial point of view because the yield of urethane is low even if mononitro compounds are used as the main starting material, and the use of dinitro compounds results in still lower yields.

Moreover, a process is known which used a catalytic system composed of palladium and a Lewis acid (U.S. Pat. No. 3,531,512). In this process, urethanes can be obtained in fairly high yield of 80-90% even by using dinitro compounds as the main starting material. In order to attain such a high yield, however, it is necessary to carry out the urethanation reaction under such severe reaction conditions as an initial carbon monoxide pressure of 190-350 kg/cm² and a temperature of 190°-200° C. In addition, the process has an industrially serious drawback in that the Lewis acid, e.g. ferric chloride, used as the promoter exerts a considerable corrosive action on metallic materials such as iron, stainless steel, and the like. Consequently, it is essential to use a reactor made of or lined with glass or tantalum in order to realize the process industrially. However, the use of a glass or tantalum reactor under the above-mentioned high temperature and pressure conditions poses further technical and economical problems.

Thus, all of these processes use a catalyst consisting of a platinum metal and/or a compound thereof and occasionally a promoter consisting of a Lewis acid and/or a Lewis acid-containing compound, but the above-mentioned difficulties including the low yield of the desired product, the use of severe reaction conditions, and the corrosion of the reactor by the catalyst have kept them from industrial practice.

SUMMARY OF THE INVENTION

Accordingly, it is the primary object of this invention to provide an improved process for preparing aromatic urethanes wherein high yields of the desired product can be obtained at a high reaction rate, or in a short reaction time.

In accordance with this invention, there is provided a process for preparing an aromatic urethane which comprises reacting an aromatic nitro compound, a hydroxyl-containing compound, and carbon monoxide at elevated temperature and pressure in the presence of a catalytic system composed of a catalyst consisting of a platinum metal, a platinum metal compound, and/or a platinum metal compound-containing compound and a promoter consisting of a Lewis acid and/or a Lewis acid-containing compound, wherein the improvement comprises adding an organic primary amino compound, a urea compound, a biuret compound, an allophanate compound, or a mixture thereof to the reaction system.

The aforesaid organic primary amino compound may be any of the compounds represented by the formula

$$R_oNH_2 \qquad (I)$$

In the above formula (I), $R_o$ represents a linear or branched alkyl group containing from 1 to 16 carbon atoms, a cycloalkyl group of 6 carbon atoms with or without an alkyl substituent containing from 1 to 3 carbon atoms, an aryl group with or without at least one alkyl substituent containing from 1 to 6 carbon atoms, and these alkyl, cycloalkyl and aryl groups may further have at least one halogen, aryl, alkenyl, cyano, nitro, alkoxy, phenoxy, thioalkoxy, thiophenoxy, carbalkoxy, carbamate, carbamyl, carbaryloxy or thiocarbamyl substituent.

The aforesaid urea compound, biuret compound, and allophanate compound may be any of the compounds represented, respectively, by the formulae

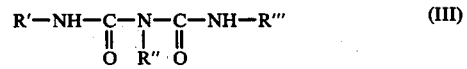

In the above formulae (II), (III) and (IV), each of R', R" and R''' represents a hyrogen atom, a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl and aryl groups may further have at least one halogen, aryl, alkenyl, cyano, nitro, alkoxy, phenoxy, thioalkoxy, thiophenoxy, carbalkoxy or thiocarbanyl substituent; and $R_1$ represents a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl and aryl groups may further have at least one halogen, aryl, akenyl, nitro, alkoxy, phenoxy or carbamate substituent.

In one preferred embodiment of this invention, the urethanation reaction is carried out in the presence of a small amount of water and one or more of those organic primary amino compounds, urea compounds, biuret compounds, and allophanate compounds which can be derived from the starting aromatic compound.

More specifically, when the starting aromatic nitro compound is a compound of the formula $$A-(NO_2)x \qquad (V)$$

where A represents a substituted or unsubstituted aromatic residue of an aromatic nitro compound from which the nitro group or groups are removed and x is an integer equal to from 1 to 4, and the starting hydroxyl-containing compound is a compound of the formula $$R_1-OH \qquad (VI)$$

where $R_1$ represents a linear or branched alkyl group containing from 1 to 16 carbon atoms, a cycloalkyl group of 6 carbon atoms with or without an alkyl substituent containing from 1 to 3 carbon atoms or an aryl group with or without at least one alkyl substituent containing from 1 to 6 carbon atoms, and these alkyl, cycloalkyl and aryl groups may further include at least one halogen, aryl, alkenyl, nitro, alkoxy, phenoxy or carbamate substituent, those organic primary amino compounds, urea compounds, biuret compounds, and allophanate compounds which can be derived from the starting aromatic nitro compound are represented, respectively, by the formuale

 (VII)

 (VIII)

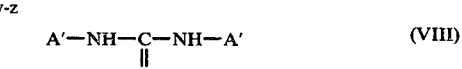 (IX)

and 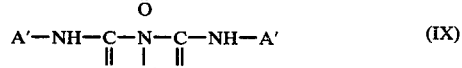 (X)

In the above formula (VII), A and x have the same meanings as defined in formula (V), $R_1$ has the same meanings as defined in formula (VI), y is an integer equal to form 1 to 4, z is an integer equal to from 0 to 3, and the sum of y and z does not exceed x. In the above formulae (VIII), (IX) and (X), A' represents a group of the formula

where A, $R_1$, x, y and z have the same meanings as defined in formula (VII).

When an organic primary amino compound, a urea compound, a biuret compound, an allophanate compound, or a mixture thereof is added to the reaction system in accordance with this invention, the desired aromatic urethane can be prepared at a higher reaction rate, or in a shorter reaction time, that that attainable by the afore-mentioned processes. Moreover, when one or more of those organic primary amino compounds, urea compounds, biuret compounds, and allophanate compounds which can be derived from the starting aromatic nitro compound are used, the yield of the desired aromatic urethane is enhanced. The yield based on the starting aromatic nitro compound can even reach a substantially theoretical level depending on the amount of the aforesaid compound or compounds added to the reaction system.

Furthermore, when a mixture or complex composed of a Lewis acid and a tertiary amine (preferably a nitrogen-containing heterocyclic compound such as pyridine) is used as the promoter, the yield is enhanced, corrosion of the reactor is suppressed, and recovery of the catalyst is facilitated, as compared with the use of Lewis acids alone.

In addition, when a small amount of water is added to the reaction system, the reaction rate is further increased without reducing the yield of the desired product.

DESCRIPTION OF THE PREFERRED EMBODIMENT

The aromatic nitro compounds useful as the main starting material in the process of the invention are those represented by the formula $$A-(NO_2)x$$

where A and x have the same meanings as defined in formula (V), and may be mononitro and polynitro compounds. They include, for example, nitrobenzene, dinitrobenzenes, dinitrotoluenes, nitronaphthalenes, nitroanthracenes, nitrobiphenyls, bis(nitrophenyl)alkanes, bis(nitrophenyl)ethers, bis(nitrophenyl)thioethers, bis(nitrophenyl)sulfones, nitrodiphenoxyalkanes, nitrophenothiazines, and heterocyclic compounds such as 5-nitropyrimidine. Specific examples of suitable nitro compounds are nitrobenzene, o-, m- and p-nitrotoluenes, o-nitro-p-xylene, 1-nitronaphthalene, m- and p-dinitrobenzenes, 2,4- and 2,6-dinitrotoluenes, dinitromesitylene, 4,4'-dinitrobiphenyl, 2,4-dinitrobiphenyl, 4,4'-dinitrodibenzyl, bis(4-nitrophenyl)methane, bis(4-nitrophenyl)ether, bis(2,4-dinitrophenyl)ether, bis(4-nitrophenyl)thioether, bis(4-nitrophenyl)sulfone, bis(4-nitrophenoxy)ethane, α,α'-dinitro-p-xylene, α,α'-dinitro-m-xylene, 2,4,6-trinitrotoluene, o-, m- and p-chloronitrobenzenes, 2,3- and 3,4-dichlonitrobenzenes, 1-chloro-2,4-dinitrobenzene, 1-bromo-4-nitrobenzene, 1-fluoro-2,4-dinitrobenzene, o-, m- and p-nitrophenyl carbamate, o-, m- and p-nitroanisoles, 2,4-dinitrophenetole, ethyl p-nitrobenzoate, m-nitrobenzenesulfonyl chloride, 3-nitrophthalic anhydride, 3,3'-dimethyl- 4,4'-dinitrobiphenyl, 1,5-dinitronaphthalene, etc., and isomers and homologues of the foregoing. These aromatic nitro compounds may be used alone or in combination. In addition, the azo and azoxy derivatives of these aromatic nitro compounds are also useful.

Among the above-enumerated aromatic nitro compounds, mononitro compounds such as nitrobenzene, o-, m- and p-chloronitrobenzenes, 2,3- and 3,4-dichloronitrobenzenes, etc. and dinitro compounds such as m- and p-dinitrobenzenes, 2,4-and 2,6-dinitrotoluenes, 1,5-dinitronaphthalene, etc. are preferred because they can be readily reacted with other reactants to give high yields of desired products which have wide applications in the manufacture of drugs, agricultural chemicals, polyurethanes, and the like.

The hydroxyl-containing compounds useful in the process of the invention are those represented by the formula

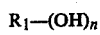

$$R_1\text{—}(OH)_n$$

where $R_1$ has the same meanings as defined in formula (VI), and n is an integer equal to or greater than 1 and preferably in the range of from 1 to 3. They include monohydric and polyhydric alcohols having one or more hydroxyl groups attach to primary, secondary or tertiary carbon atoms, as well as monohydric and polyhydric phenols.

Specific examples of suitable alcohols are monohydric alcohols such as methyl alcohol, ehtyl alcohol, n- and isopropyl alcohols, n-, iso- and t-butyl alcohols, linear or branched amyl alcohol, hexyl alcohol, cyclohexyl alcohol, lauryl alcohol, cetyl alcohol, benzyl alcohol, chlorobenzyl alcohol, methoxybenzyl alcohol, etc.; dihydric alcohols such as ethylene glycol, diethylene glycol, propylene glycol, dipropylene glycol, etc.; trihydric alcohols such as glycerol, hexanetriol, etc.; and further polyhydric alcohols.

Specific examples of suitable phenols are phenol, chlorophenol, cresol, ethylphenol, linear or branched propylphenol, butyl- and higher alkylphenols, catechol, resorcinol, 4,4'-dihydroxydiphenylmethane, 2,2'-isopropylidenediphenol, anthranol, phenanthrol, pyrogallol, phloroglucinol, etc.

Among the above-enumerated hydroxyl-containing compounds, methyl alcohol, ethyl alcohol, and isobutyl alcohol are preferred because they give higher yields of desired products at a higher reaction rate as compared with other hydroxyl-containing compounds.

The catalysts useful in the process of the invention include, for example, elemental palladium, rhodium and ruthenium; the halides, cyanides, thiocyanides, isocyanides, oxides, sulfates, nitrates and carbonyl compounds of these metals; the addition products or complexes of these compounds with tertiary amines such as triethylamine, pyridine, isoquinoline, etc. and the complexes of these compounds with organic phosphorus compounds such as triphenylphosphine, etc.; and mixtures of the foregoing. These catalysts may be used either by adding them directly to the reaction system or by associating them with carriers such as alumina, silica, carbon, barium sulfate, calcium carbonate, asbestos, bentonite, diatomaceous earth, fullers's earth, organic ion exchange resins, inorganic ion exchange resins, magnesium silicate, aluminum silicate, molecular sieve, and the like and then adding them to the reaction system. Furthermore, these carriers may be added to the reaction system separately from the catalysts including elemental palladium, rhodium and ruthenium as well as compounds thereof.

Among the above-enumerated catalysts, elemental palladium and palladium compounds are preferred. Specific examples are elemental palladium, palladium chloride, palladium bromide, and elemental palladium associated with a carrier such as carbon or alumina.

The Lewis acids useful as the promoter in the process of the invention are, for example, those described in Jack Hine: "Physical Organic Chemistry" (McGrow-Hill Book Co., New York, 1962) and imply Br∅nsted acids. They include, for example, the halides, sulfates, acetates, phosphates, and nitrates of metals such as tin, titanium, germanium, aluminum, iron, nickel, zinc, cobalt, manganese, thallium, zirconium, copper, lead, vandium, niobium, tantalum, mercury, etc.

Specific examples of suitable Lewis acids are ferric chloride, ferrous chloride, stannic chloride, aluminum chloride, cupric chloride, cuprous chloride, copper acetate, etc.

Lewis acid-containing compounds and mixtures of Lewis acids and Lewis acid-containing compounds are also useful as the promoter in the process of the invention. The aforesaid Lewis acid-containing compounds include, for example, complexes derived from Lewis acids and tertiary amines. Specific examples of the complex-forming tertiary amines are triethylamine, N,N-diethylaniline, N,N-diethylcyclohexylamine, 1,4-diazabicyclo[2,2,2]octane, pyridine, picoline, isoquinoline, quinoline, etc.

Among the above-enumerated tertiary amines, nitrogen-containing heterocyclic compounds such as pyridine, picoline and isoquinoline are preferred. The use of a complex derived from such a nitrogen-containing heterocyclic compound and a Lewis acid prevents the corrosion of the reactor by the Lewis acid, enhances the yield of the desired product, and facilitates recovery of the catalyst, as compared with the use of the Lewis acid alone.

Furthermore, complexes derived from Lewis acids and organic phosphorus compounds are also useful. Specific examples of suitable organic phosphorus compounds are phosphines such as triphenylphosphine, dimethylphenylphosphine, bis-diphenylphosphinoethane, etc. The components of such a complex may be added to the reaction system separately from each other, though the use of a previously formed complex is more effective.

Where a nitrogen-containing heterocyclic compound as described above is used in combination with a Lewis acid, the reaction rate is further increased by addding a small amount of water to the reaction system. The amount of water added should be from 1 to 70 moles and preferably from 10 to 50 moles per mole of the starting aromatic nitro compound. If the amount is less than 1 mole, the addition of water will be virtually ineffective, while if the amount is more than 70 moles, the yield of the desired product will be greatly reduced.

The organic primary amino compounds useful in the process of the invention include, for example, methylamine, ethylamine, propylamine, butylamine, pentylamine, hexylamine, ethylenediamine, propylenediamine, butylenediamine, hexanediamine, cyclohexylamine, cyclohexyldiamine, aniline, o-, m- and p-diaminobenzenes, 2-amino-4-carbamatetoluene, 4-amino-2-carbamatetoluene, 2-amino-6-carbamatetoluene, o-, m- and p-nitroanilines, 4-nitro-2-aminotoluene, 2-nitro-4-aminotoluene, 2-nitro-6-aminotoluene, 3-nitro-4- aminotoluene, 4-nitro-3-aminotoluene, 2-nitro-3-aminotoluene, 3-nitro-2-aminotoluene, o-and p-phenylenediamine, benzylamine, o-amino-p-xylene, 1-aminophthalene, 2,4- and 2,6-diaminotoluenes, diaminomesitylene, 4,4'-diaminodibenzyl, bis(4-aminophenyl)methane, bis(4-aminophenyl)ether, bis(2,4-diaminophenyl)ether, bis(4-aminophenyl)thioether, bis(4-aminophenyl)sulfone, bis(4-aminophenoxy)ethane, $\alpha,\alpha'$-diamino-p-xylene, $\alpha,\alpha'$-diamino-m-xylene, 2,4,6-triaminotoluene, o-, m- and p-chloroanilines, 1-chloro-2,4-diaminobenzene, p-bromoaniline, 1-fluoro-2,4-diaminobenzene, 2,4-diaminophenetole, o-, m- and p-aminoanisoles, ethyl p-aminobenzoate, 3-aminophthalic anhydride, 3,3'-dimethyl-4,4'-diaminobiphenyl, 4-amino-4'-nitrodiphenylmethane, 1-amino-5-nitronaphthalene, etc., and isomers and homologues of the foregoing. These aromatic amino compounds may be used alone or in combination.

Among the above-enumerated aromatic amino compounds, those which can be derived from the starting aromatic nitro compound are preferred. For example, when nitrobenzne is used as the starting aromatic nitro compound, aniline is preferred. Similarly, 2-amino-4-nitrotoluene, 4-amino-2-nitrotoluene, 2-amino-4-carbamatetoluene, 4-amino-2-carbamatetoluene, and 2,4-diaminotoluene are preferably used when the starting aromatic nitro compound is 2,4-dinitrotoluene, while 2-amino-6-nitrotoluene, 2-amino-6-carbamatetoluene, and 2,6-diaminotoluene are preferably used when the starting aromatic nitro compound is 2,6-dinitrotoluene.

The urea compounds, biuret compounds, and allophanate compounds useful in the process of the invention are those represented by the respective formulae (VIII), (IX) and (X) in which, for example, A' is a phenyl group when the starting aromatic nitro compound is nitrobenzene or a tolyl group having a nitro, amino or carbamate group when the starting aromatic nitro compound is dinitrotoluene.

No particular limitation is placed on the amount of organic primary amino compound, urea compound, biuret compound, and/or allophanate compound used. However, they are preferably used in an amount equal to from 0.1 to 100 moles per mole of the nitro group of the starting aromatic nitro compound. The process of the invention may be carried out in the absence of solvent, but the use of a solvent is not precluded. Suitable solvents include, for example, aromatic solvents such as benzene, toluene, xylene, etc.; nitriles such as acetonitrile, benzonitrile, etc.; sulfones such as sulfolane, etc.; halogenated aliphatic hydrocarbons such as 1,1,2-trichloro-1,2,2-trifluoroethane, etc.; halogenated aromatic hydrocarbons such as monochlorobenzene, dichlorobenzene, trichlorobenzene, etc.; ketones; esters; and other solvents such as tetrahydrofuran, 1,4-dioxane, 1,2-dimethoxyethane, etc.

In carrying out the process of the invention, the hydroxyl-containing compound and carbon monoxide are preferably used in amounts equal to at least 1 mole per mole of the nitro group of the starting aromatic nitro compound.

The amount of platinum metal or platinum metal compound used as the catalyst may vary widely according to the type thereof and other reaction conditions. However, on a weight basis, the amount of catalyst is generally in the range of from $1\times10^{-5}$ to 1 part, and preferably from $1\times10^{-4}$ to $5\times10^{-1}$ part, per part of the starting aromatic nitro compound when expressed in terms of its metallic component.

Similarly, on a weight basis, the amount of Lewis acid used as the promoter is generally in the range of from $2\times10^{-3}$ to 2 parts, and preferably from $5\times10^{-2}$ to 1 part, per part of the starting aromatic nitro compound.

The reaction temperature is generally held in the range of from 80° to 230° C., and preferably from 140° to 200° C.

The reaction pressure, or the initial carbon monoxide pressure, is generally in the range of from 10 to 1,000 kg/cm$^2$G, and preferably from 30 to 500 kg/cm$^2$G.

The reaction time depends on the nature of aromatic nitro compound used, the reaction temperature, the reaction pressure, the type and amount of catalyst used, the type and amount of organic primary amino compound, urea compound, biuret compound, or allophanate compound added, the type of reactor employed, and the like, but is generally in the range of from 5 minutes to 6 hours. After completion of the reaction, the reaction mixture is cooled and the gas is discharged from the reactor. Then, the reaction mixture is subjected to any conventional procedure including filtration, distillation, or other suitable separation steps, whereby the resulting urethane is separated from any unreacted materials, any by-products, the solvent, the catalyst, and the like.

The urethanes prepared by the process of the invention have wide applications in the manufacture of agricultural chemicals, isocyanates, and polyurethanes.

This invention is more fully illustrated by the following examples. However, they are not to be construed to limit the scope of the invention. In all of these examples, the reaction was carried out in an electromagnetic stirring type autoclave made of stainless steel (SUS 32). The yields shown in these examples were calculated from the results of analysis by gas chromatography and liquid chromatography.

EXAMPLE 1

Into an autoclave having a capacity of 200 ml were charged 8.4 g of nitrobenzene, 68 ml of ethanol, 0.0086 g of palladium chloride, 1.86 g of ferrous chloride-pyridine complex (formed by dissolving ferrous chloride and pyridine in ethanol and mixing them in a molar ratio of 1:2), 0.29 g of water, and 0.6 g of aniline. The air in the autoclave was replaced by nitrogen gas. Then, carbon monoxide was introduced into the autoclave until an initial pressure of 50 kg/cm$^2$G was established. The reaction mixture was heated with stirring and held at 165° C. for 40 minutes. After completion of the reaction, the reaction mixture was cooled to room temperature and the gas was discharged from the autoclave. Analysis of the resulting solution revealed that the yield of urethane (ethyl n-phenylcarbamate) was 100% based on the charged nitrobenzene.

EXAMPLE 2 AND CONTROL 1

The procedure of Example 1 was repeated except that the aniline was replaced by 0.7 g of diphenylurea (Example 2). In addition, the procedure of Example 1 was repeated except that the aniline was omitted (Control 1). The results of Example 2 and Control 1, together with those of Example 1, are summarized in Table 1 below.

Table 1

|  | Additive | Amount (g) | Reaction Time (min.) | Yield of Urethane (%) |
|---|---|---|---|---|
| Example 1 | Aniline | 0.6 | 40 | 100 |

Table 1-continued

| | Additive | Amount (g) | Reaction Time (min.) | Yield of Urethane (%) |
|---|---|---|---|---|
| 2 | Diphenylurea | 0.7 | 40 | 100 |
| Control 1 | — | — | 60 | 95 |

EXAMPLE 3

Into an autoclave having a capacity of 200 ml were charged 12.39 g of 2,4-dinitrotoluene, 68 ml of ethanol, 0.0086 g of palladium chloride, 3.71 g of ferrous chloride-pyridine complex, 0.29 g of water, and 1.2 g of isopropylamine. The air in the autoclave was replaced by nitrogen gas. The, carbon monoxide was introduced into the autoclave until an initial pressure of 90 kg/cm$^2$G was established. The reaction mixture was heated with stirring and held at 165° C. for 110 minutes until the pressure ceased to drop. After completion of the reaction, the reaction mixture was cooled to room temperature and the gas was discharged from the autoclave. Analysis of the resulting solution revealed that the starting 2,4-dinitrotoluene and the intermediate mononitromonoethylcarbamatetoluene (hereinafter referred to simply as "mononitromonourethane") were absent and that the yield of 2,4-diethylcarbamatetoluene (hereinafter referred to simply as "diurethane") was 92% based on the charged 2,4-dinitrotoluene.

EXAMPLES 4–11 AND CONTROL 2

The procedure of Example 3 was repeated except that the isopropylamine was replaced by a variety of primary amino compounds and urea compounds (Examples 4–11). In addition, the procedure of Example 3 was repeated except that the isopropylamine was omitted (Control 2). The results of Examples 4–11 and Control 2 are summarized in Table 2 below.

| | Additive | Amount (g) | Reaction Time (min.) | Yield of diurethane (%) |
|---|---|---|---|---|
| Example 3 | Isopropylamine | 1.2 | 110 | 92 |
| 4 | Aniline | 1.9 | 110 | 93 |
| 5 | Urea | 0.6 | 140 | 93 |
| 6 | Diphenylurea | 2.1 | 150 | 93 |
| 7 | 2-amino-4-nitrotoluene | 0.3 | 180 | 98 |
|   | 4-amino-2-nitrotoluene | 0.3 | | |
| 8 | 2-amino-4-nitrotoluene | 2.5 | 150 | 138 |
|   | 4-amino-2-nitrotoluene | 2.5 | | |
| 9 | 2-amino-4-ethylcarbamatetoluene | 1.3 | 160 | 110 |
|   | 4-amino-2-ethylcarbamatetoluene | 1.3 | | |
| 10 | 1-(3-ethylcarbamate-4-methylphenyl)-3-(2-methyl-5-ethylcarbamatephenyl)urea | 1.4 | 180 | 98 |
| 11 | 1-(3-ethylcarbamate-4-methylphenyl)-3-(2-methyl-5-ethylcarbamatephenyl)urea | 4.2 | 160 | 110 |
| Control 2 | — | — | 200 | 92 |

EXAMPLE 12

The procedure of Example 3 was repeated except that the ethanol was replaced by 68 ml of isobutanol and the isopropylamine was replaced by 0.8 g of 2-amino-4-isobutylcarbamatetoluene and 0.8 g of 4-amino-2-isobutylcarbamatetoluene. After 160 minutes of reaction, the yield of diurethane was 99%.

EXAMPLE 13

Into an autoclave having a capacity of 200 ml were charged 6.0 g of 2,4-dinitrotoluene, 48 ml of ethanol, 0.51 g of 5% palladium-alumina, 1.38 g of ferric chloride, 2.01 g of pyridine, 0.16 g of 2-amino-4-ethylcarbamatetoluene, and 0.16 g of 4-amino-2-ethylcarbamatetoluene. The air in the autoclave was replaced by nitrogen gas. Then, carbon monoxide was introduced into the autoclave until an initial pressure of 70 kg/cm$^2$G was established. The reaction mixture was heated with stirring and held at 160° C. for 120 minutes. Analysis of the resulting solution revealed that the yield of diurethane was 100% based on the charged 2,4-dinitrotoluene.

CONTROL 3

The procedure of Example 13 was repeated except that the aminoethylcarbamatetoluenes were omitted. The reaction was carried out for the same period of time, or 120 minutes, as in Example 13. Analysis of the resulting solution revealed that the starting 2,4-dinitrotoluene was absent but the yield of mononitromonourethane was 15% and that of diurethane was 80%.

Under the same conditions, the reaction was carried out until the absorption of carbon monoxide ceased. After 150 minutes of reaction, the yield of diurethane was 94%.

EXAMPLE 14

Into an autoclave having a capacity of 200 ml were charged 6.0 g of 2,4-dinitrotoluene, 48 ml of ethanol, 0.51 g of 5% palladium-alumina, 1.38 g of ferric chloride, 2.01 g of pyridine, and 1.4 g of an allophanate compound (formed by heating an equimolar mixture of 2,4-diethylcarbamatetoluene and 2,4-diisocyanatotoluene). After an initial pressure of 70 kg/cm$^2$G was established, the reaction mixture was held at 165° C. for 120 minutes. Analysis of the resulting solution revealed that the yield of diurethane was 98%.

EXAMPLE 15

The procedure of Example 14 was repeated except that the allophanate compound was replaced by 1.4 g of a biuret compound (formed by heating a mixture of 2,4-toluene diisocyanate and water). The absorption of carbon monoxide ceased in 120 minutes. Analysis of the resulting solution revealed that the yield of diurethane was 97%.

What is claimed is:

1. In a process for preparing an aromatic urethane which comprises reacting at temperature in the range of 80°-230° C. pressures in the range of 10–1000 Kg/cm$^2$G for a time ranging from 5 minutes to 6 hours an aromatic nitro compound, an organic hydroxyl-containing compound having at least one hydroxyl group, and carbon monoxide in the presence of a catalyst selected from the group consisting of platinum, palladium, rhodium or ruthenium metal or a compound thereof and mixtures thereof and a promoter selected from the group consisting of Lewis acids, Lewis acid-containing compounds and mixtures thereof, the improvement which comprises adding to the reaction system at least one compound selected from the group consisting of an organic primary amino compound of the formula $$R_oNH_2 \qquad (I)$$

where $R_o$ represents a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl and aryl groups may further have at least one halogen, aryl, alkenyl, cyano, nitro, alkoxy, phenoxy, thioalkoxy, thiophenoxy, carbalkoxy, carbamate, carbamyl, carbaryloxy or thiocarbamyl substituent; a urea compound of the formula $$R'-NH-\underset{\underset{O}{\|}}{C}-NH-R'' \qquad (II)$$

where each of R' and R'' represents a hydrogen atom, a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl and aryl groups may further have at least one halogen, aryl, alkenyl, cyano, nitro, alkoxy, phenoxy, thioalkoxy, thiophenoxy, carbalkoxy, carbamate, carbamyl carbaryloxy or thiocarbamyl substituent; a biuret compound of the formula $$R'-NH-\underset{\underset{O}{\|}}{C}-\underset{R''}{N}-\underset{\underset{O}{\|}}{C}-NH-R''' \qquad (III)$$

where each of R', R'' and R''' has the same meaning as defined for R' and R'' in formula (II); and an allophanate compound of the formula $$R'-NH-\underset{\underset{O}{\|}}{C}-\underset{R''}{N}-\underset{\underset{O}{\|}}{C}-OR_1 \qquad (IV)$$

where each of R' and R'' has the same meaning as defined for R' and R'' in formula (II), $R_1$ represents a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl and aryl groups may further have at least one halogen, aryl, alkenyl, nitro, alkoxy, phenoxy or carbamate substituent.

2. The process according to claim 1 wherein said organic primary amino compound is aniline.

3. The process according to claim 1 wherein said urea compound is urea.

4. The process according to claim 1 wherein said aromatic nitro compound is nitrobenzene.

5. The process according to claim 1 wherein said aromatic nitro compound is dinitrotoluene.

6. The process according to claim 1 wherein said organic hydroxyl-containing compound is ethyl alcohol.

7. The process according to claim 1 wherein said organic hydroxyl-containing compound is isobutyl alcohol.

8. The process according to claim 1 wherein said catalyst is elemental palladium, a palladium compound, a palladium compound-containing compound, or a mixture thereof.

9. The process according to claim 1 wherein said promoter is ferrous chloride, a ferrous chloride-containing compound, or a mixture thereof.

10. The process according to claim 1 wherein said promoter is ferric chloride, a ferric chloride-containing compound, or a mixture thereof.

11. The process according to claim 1 wherein said promoter is a complex composed of ferrous chloride and a nitrogen-containing heterocyclic compound.

12. The process according to claim 11 wherein water is added to the reaction system in an amount equal to from 1 to 100 moles per mole of the starting aromatic nitro compound.

13. In a process for preparing an aromatic urethane which comprises reacting, at a temperature of 80°-230° C., a and pressure, of 10-1000 Kg/cm²G and for a time of from 5 min. to 6 hours an aromatic nitro compound of the formula $$A-(NO_2)_x \qquad (V)$$

where A represents a substituted or unsubstituted aromatic residue of an aromatic nitro compound from which the nitro group or groups are removed an x is an integer equal to from 1 to 4, an organic hydroxyl-containing compound of the formula $$R_1-OH \qquad (VI)$$

where $R_1$ represents a linear or branched alkyl group containing from 1 to 16 carbon atoms, a cycloalkyl group of 6 carbon atoms with or without an alkyl substituent containing from 1 to 3 carbon atoms, or an aryl group with or without at least one alkyl substituent containing from 1 to 6 carbon atoms, and these alkyl, cycloalkyl, and aralkyl groups may further have a halogen, aryl, alkenyl, nitro, alkoxy, phenoxy or carbamate substituent, and carbon monoxide in the presence of a catalyst selected from the group consisting of platinum, palladium, rhodium or ruthenium metal or a compound thereof and mixtures thereof and a promotor selected from the group consisting of Lewis acids, Lewis acid-containing compounds, and mixtures thereof, the improvement which comprises adding to the reaction system at least one compound selected from the group consisting of an aromatic primary amino compound of the formula $$A\begin{matrix}\diagup(NH_2)_y\\-(NHCO_2R_1)_z\\ \diagdown(NO_2)_{x-y-z}\end{matrix} \qquad (VII)$$

where A and x have the same meanings as defined in formula (V), $R_1$ has the same meaning as defined in formula (VI), y is an integer equal to from 1 to 4, z is an integer equal to from 0 to 3, and the sum of y and z does not exceed x; a urea compound of the formula

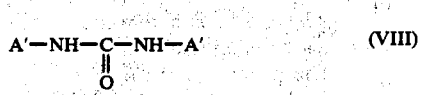

where A' represents a group of the formula

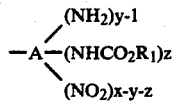

and A, $R_1$, x, y and z have the same meanings as defined in formula (VII); a biuret compound of the formula

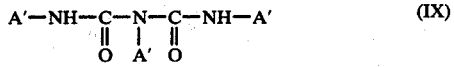

where A' has the same meaning as defined in formula (VIII); and an allophanate compound of the formula

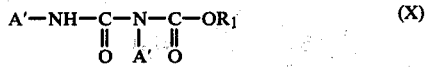

where A' has the same meaning as defined in formula (VIII) and $R_1$ has the same meaning as defined in formula (VI).

14. The process according to claim 13 wherein A in formula (V) is a phenyl group and $R_1$ in formula (VI) is an ethyl or isobutyl group.

15. The process according to claim 13 wherein A in formula (V) is a tolyl group having a nitro, amino or carbamate group and $R_1$ in formula (VI) is an ethyl or isobutyl group.

16. The process according to claim 13 wherein said catalyst is elemental palladium, a palladium compound, palladium compound-containing compound, a mixture thereof.

17. The process according to claim 13 wherein said promoter is ferrous chloride, a ferrous chloride-containing compound, or a mixture thereof.

18. The process according to claim 13 wherein said promoter is ferric chloride, a ferric chloride-containing compound, or a mixture thereof.

19. The process according to claim 13 wherein said promoter is a complex composed of ferrous chloride and a nitrogen-containing heterocyclic compound.

20. the process according to claim 19 wherein water is added to the reaction system in an amount equal to from 1 to 100 moles per mole of the starting aromatic nitro compound.

21. The process according to claim 20 wherein said catalyst is elemental palladium, a palladium compound, a palladium compound-containing compound, or a mixture thereof and said promoter is a complex of ferrous chloride and a nitrogen-containing heterocyclic compound.

22. The process according to claim 1 wherein said organic nitro compound is selected from the group consisting of nitro-benzene, o-, m- and p-nitrotoluenes, m- and p-dinitrobenzenes, 2, 4- and 2,6-dinitrotoluenes, bis-(4-nitrophenyl) methane, bis-(4-nitrophenyl) ether, o-, m- and p-chloronitrobenzenes, 2, 3- and 3,4-dichloronitrobenzenes, and 1,5-dinitronaphthalene.

23. The process according to claim 1 wherein said organic hydroxyl containing compound is selected from the group consisting of methyl alcohol, ethyl alcohol, n- and iso-propyl alcohols, and n-, iso- and tert-butyl alcohols.

24. The process according to claim 1 wherein said catalyst is selected from the group consisting of elemental palladium; halides, cyanides, thiocyanides, isocyanides, oxides, sulfates, nitrates and carbonyl compounds of palladium; and an addition product or complex of palladium compound with a tertiary amine.

25. The process according to claim 1 wherein said promotor is selected from the group consisting of ferrous chloride, ferric chloride and the complex thereof with a tertiary amine selected from pyridine, picoline, isoquinoline, quinoline and triethyl amine.

26. The process according to claim 1 wherein said organic primary amine compound is selected from the group consisting of methylamine, ethylamine, n- and iso-propylamines, butylamine, cyclohexylamine, aniline, o-, m-, and p-diaminobenzenes, 2-amino-4-carbamatetoluene, 4-amino-2-carbamatetoluene, 2-amino-6-carbamatetoluene, o-, m- and p-nitroanilines, 4-nitro-2-aminotoluene, 2-nitro-4-aminotoluene, 2-nitro-6-aminotoluene, 3-nitro-4-aminotoluene, o- and p-phenylenediamines, 2,4- and 2,6-diaminotoluenes, and o-, m- and p-chloroanilines.

27. The process according to claim 1 wherein R', R" and R'" in formulas (II), (III) and (IV) are independently hydrogen atom, methyl or phenyl, and $R_1$ in formula (IV) is selected from the group consisting of methyl, ethyl, n- and iso-propyl, and n-, iso- and tert-butyl.

28. The process according to claim 1 wherein said aromatic compound is nitrobenzene, dinitrobenzene or dinitrotoluene; said organic hydroxyl-containing compound is ethyl alcohol or isobutyl alcohol; said catalyst system is composed of a catalyst selected from elemental palladium, a palladium compound, an addition compound or a complex thereof with a tertiary amine and a mixture thereof and a promotor selected from ferrous chloride, ferric chloride, a complex thereof with prydine, picoline, quinoline, isoquinoline or triethylamine and a mixture thereof; and said compound added to the reaction system is selected from the group consisting of an organic primary amine selected from isopropylamine, aniline, 2-amino-4-nitrotoluene, 4-amino-2-nitrotoluene, 2-amino-4-ethylcarbamate toluene and 4-amino-2-ethylcarbamate toluene, a urea compound selected from urea, diphenyl urea and 1-(3-ethylcarbamate-4-methylphenyl)-3-(2-methyl-5-ethylcarbamatephenyl) urea, a biuret compound formed by heating a mixture of 2,4-toluene diisocyanate and water, and an allophanate compound formed by heating an equimolecular mixture of 2,4-diethylcarbamate toluene and 2,4-diisocyanate toluene.

29. The process according to claim 13 wherein said catalyst is selected from the group consisting of elemental palladium; halides, cyanides, thiocyanides, isocyanides, oxides, sulfates, nitrates and carbonyl compounds of palladium; and an addition product or complex of a palladium compound with a tertiary amine.

30. The process according to claim 13 wherein said promotor is selected from the group consisting of ferrous chloride, ferric chloride and the complex thereof with a tertiary amine selected from pyridine, picoline, isoquinoline, quinoline and triethyl amine.

31. The process according to claim 13 wherein A in formula (V) is selected from the group consisting of phenyl, o-, m- and p-chlorophenyl, and o-, m- and p-tolyl groups.

32. The process according to claim 13 wherein $R_1$ in formula (VI) is selected from the group consisting of methyl, ethyl, n- and iso-propyl, and n-, iso- and tert-butyl groups.

33. The process according to claim 13 wherein said compound of formula (V) is nitrobenzene, dinitrobenzene or dinitrotoluene; and said compound of formula (VI) is an ethyl alcohol or isobutyl alcohol; said catalyst system is composed of a catalyst selected from elemental palladium, a palladium compound, an addition product or a complex thereof with a tertiary amine and a mixture thereof and a promotor selected from ferrous chloride, ferric chloride, a complex thereof with pyridine, picoline, quinoline, isoquinoline or triethylamine and a mixture thereof; and said compound added to the reaction system is selected from the group consisting of an organic primary amine selected from aniline, 2-amino-4-nitrotoluene, 4-amino-2-nitrotoluene, 2-amino-4-ethylcarbamate toluene and 4-amino-2-ethylcarbamate toluene, a urea compound selected from diphenyl urea and 1-(3-ethylcarbamate-4-methylphenyl)-3-(2-methyl-5-ethylcarbamatephenyl) urea, a biuret compound formed by heating a mixture of 2,4-toluene diisocyanate and water, and an allophanate compound formed by heating an equimolecular mixture of 2,4-diethylcarbamate toluene and 2,4-diisocyanate toluene.

34. The process according to claim 1 wherein said compound added to the reaction system is selected from the group consisting of an organic primary amine selected from isopropylamine, aniline, 2-amino-4-nitrotoluene, 4-amino-2-nitrotoluene, 2-amino-4-ethylcarbamate toluene and 4-amino-2-ethylcarbamate toluene, and a urea compound selected from urea, diphenyl urea and 1-(3-ethylcarbamate-4-methylphenyl)-3-(2-methyl-5-ethylcarbamatephenyl) urea.

35. The process according to claim 13 wherein said compound added to the reaction system is selected from the group consisting of an organic primary amine selected from aniline, 2-amino-4-nitrotoluene, 4-amino-2-nitrotoluene, 2-amino-4-ethylcarbamate toluene and 4-amino-2-ethylcarbamate toluene, and a urea compound selected from diphenyl urea and 1-(3-ethylcarbamate-4-methylphenyl)-3-(2-methyl-5-ethylcarbamatephenyl) urea.

36. The process according to claim 13 wherein said aromatic compound is nitrobenzene; said organic hydroxyl-containing compound is ethyl alcohol; said catalyst system is composed of palladium chloride and a ferrous chloride-pyridine complex; and said compound added to the reaction system is aniline.

37. The process according to claim 13 wherein said aromatic compound is dinitrobenzene; said organic hydroxyl-containing compound is ethyl alcohol; said catalyst system is composed of palladium chloride and a ferrous chloride-pyridine complex; and said compound added to the reaction system is 2-amino-4-ethylcarbamate toluene, 4-amino-2-ethylcarbamate toluene and a mixture thereof.

38. The process according to claim 13 wherein said aromatic compound is 2,4-dinitrotoluene; said organic hydroxyl-containing compound is ethyl alcohol; said catalyst system is composed of palladium chloride and a ferrous chloride-pyridine complex; and said compound added to the reaction system is 2-amino-4-nitrotoluene, 4-amino-2-nitrotoluene, a mixture thereof, or 2-amino-4-ethylcarbamate toluene, 4-amino-2-ethylcarbamate or a mixture thereof.

* * * * *